(12) United States Patent
Gabr et al.

(10) Patent No.: US 9,988,348 B1
(45) Date of Patent: Jun. 5, 2018

(54) SYNTHESIS AND ANTIMICROBIAL USE OF A TRITHIOCARBONATE DERIVATIVE

(71) Applicant: KING SAUD UNIVERSITY, Riyadh (SA)

(72) Inventors: Yahia Nasser Mabkhot Gabr, Riyadh (SA); Jamal Mohammed Ali Khaled, Riyadh (SA); Mujeeb Abdullah Saeed Sultan, Riyadh (SA); Salim S. Al-Showiman, Riyadh (SA); Naiyf Sultan Helial Alaloi Alharbi, Riyadh (SA); Hazem Ahmed Ghabbour, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days. days.

(21) Appl. No.: 15/615,765

(22) Filed: Jun. 6, 2017

(51) Int. Cl.
*C07C 329/00* (2006.01)
*A61K 31/265* (2006.01)

(52) U.S. Cl.
CPC .......... *C07C 329/00* (2013.01); *A61K 31/265* (2013.01); *A61K 2121/00* (2013.01)

(58) Field of Classification Search
CPC .................................................... C07C 329/00
See application file for complete search history.

(56) References Cited

U.S. PATENT DOCUMENTS

| 7,423,161 B2 | 9/2008 | Zard et al. |
| 7,495,128 B2 | 2/2009 | Lai et al. |
| 8,791,286 B2 | 7/2014 | Yodice et al. |

OTHER PUBLICATIONS

Derivative, 2017, https://en.wikipedia.org/wiki/Derivative_(chemistry).*
Soleiman-Beigi et al., 2014, Journal of Sulfur Chemistry, 35(5), 470-476.*

* cited by examiner

*Primary Examiner* — Sun Jae Yoo
(74) *Attorney, Agent, or Firm* — Richard C. Litman

(57) ABSTRACT

A method for preparing a trithiocarbonate derivative compound includes reacting ethyl cyanoacetate, carbon disulfide ($CS_2$) and ethyl chloroacetate in the presence of potassium carbonate ($K_2CO_3$) in an organic solvent to produce 2,2'-(thiocarbonylbis(sulfanediyl))diacetate compound, represented by the structural formula:

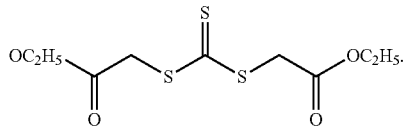

4 Claims, 4 Drawing Sheets

SYNTHESIS AND ANTIMICROBIAL USE OF A TRITHIOCARBONATE DERIVATIVE

BACKGROUND OF THE INVENTION

1. Field of the Invention

The present invention relates to anti-microbial drugs, and particularly to synthesis of a trithiocarbonate derivative for use as anti-microbial agents.

2. Description of the Related Art

Various synthetic routes have been employed for synthesis of trithiocarbonates. Trithiocarbonates can be simply and efficiently incorporated into many organic compounds and pharmaceutical therapeutic agents. In organic synthesis, for instance, trithiocarbonates have been employed in surface and colloidal nanotechnology, as reagents for platinum group metals flotation, electrolyte additive in lithium batteries, monodisperse surface modification, and polymers formation. Trithiocarbonates also represent a promising class of pharmaceutical therapeutic agents or biologically active compounds, as they can act as biological toxicants, anti-radiation in mice, antitumor agents inhibitors for carbonic anhydrase, as well provide anti-glaucoma effects in vivo.

There is no doubt that many microbial pathogens are increasingly developing resistance to antimicrobial drugs. Antimicrobial agents must kill or inhibit specific targets in pathogenic microorganisms which typically exist in an essential pathway of the microbial pathogen. Ideally, antimicrobial agents are easily evaluated in vitro and in vivo, specific for the pathogenic microorganism, non-toxic for animals and/or humans, and do not result in the quick gaining of resistance.

Broad spectrum antimicrobials have advantages in the initial empirical therapy especially against serious microbial infections. For severe microbial diseases, a therapy must be administered before identification of the pathogenic microbe because the time of diagnosis is a powerful predictor of mortality. The patents of novel anti-fungal drugs include azole compounds (new imidazole, fuconazole analogs, azole with 2,6-di-tert-butyl-4-methylphenol), enzymes inhibitors (chitin inhibitors, β-1,3-D-glucan synthases inhibitors), peptides (fusion peptides), phenylalkane nitriles (esters of 2-phenylalkane nitriles), boron compounds, pyridine derivatives, cyclic guanidines and quinolinium compounds, arylalkyl (azole derivatives in the structure of oxime ester.

Thus, synthesis of trithiocarbonate derivatives possessing antibacterial and antifungal properties solving the aforementioned problems is desired.

SUMMARY OF THE INVENTION

A method for preparing a trithiocarbonate derivative compound includes reacting ethyl cyanoacetate, carbon disulfide ($CS_2$) and ethyl chloroacetate in the presence of potassium carbonate ($K_2CO_3$) in an organic solvent to produce 2,2'-(thiocarbonylbis(sulfanediyl))diacetate compound, represented by the structural formula:

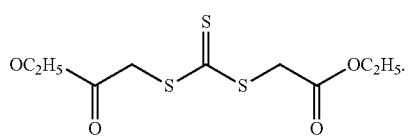 [SMILES: CCOC(=O)CSC(=S)SCC(=O)OCC]

A method for administering an antimicrobial composition to a subject in order to inhibit the proliferation of a microbial infection or colonization can include the step of administering a therapeutically effective amount of a 2,2'-(thiocarbonylbis(sulfanediyl))diacetate compound.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

A method for preparing a trithiocarbonate derivative compound includes reacting ethyl cyanoacetate, carbon disulfide ($CS_2$) and ethyl chloroacetate in the presence of potassium carbonate ($K_2CO_3$) in an organic solvent to produce the trithiocarbonate derivative. The trithiocarbonate derivative can be 2,2'-(thiocarbonylbis(sulfanediyl))diacetate, represented by the following structural formula:

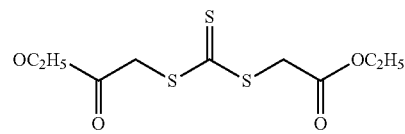 [SMILES: CCOC(=O)CSC(=S)SCC(=O)OCC]

Figure 1:
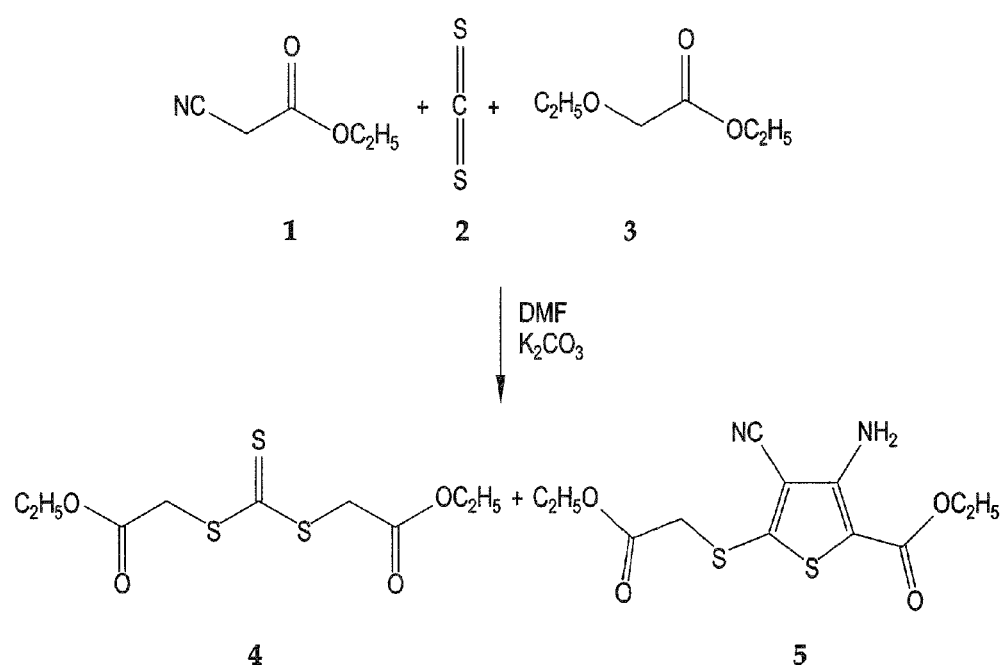
FIG. 1 shows a reaction scheme for synthesis of the trithiocarbonate derivative compound.

An exemplary synthesis method, depicted in FIG. 1, can include mixing ethyl cyanoacetate 1, carbon disulfide ($CS_2$) 2, and ethyl chloroacetate 3 in an organic solvent, such as dimethyl formamide (DMF), at room temperature to form a first mixture. Anhydrous potassium carbonate ($K_2CO_3$) can be mixed with the first mixture to form a second mixture. The second mixture can be cooled and a solid product can be precipitated by adding water. The product can be collected by filtration, washed, and dried. Ethanol (EtOH) can be added to the crude product to afford 2,2'-(thiocarbonylbis(sulfanediyl))diacetate 4 and a thiophene derivative 5. For the synthesis reaction, the molar ratio of ethyl cyanoacetate: carbon disulfide:ethyl chloroacetate can be about 1:2:2, respectively.

Although compound 4 is commercially available, it is very expensive, e.g. 5 mg costs 126.5 EUR. In comparison, the production costs of 5 mg compound 4 according to the present method costs 0.125 EUR.

A method for treating or inhibiting a microbial infection can include the step of administering to a patient in need thereof a therapeutically effective amount of a 2'-(thiocarbonylbis(sulfanediyl))diacetate compound or a pharmaceutically acceptable salt thereof. The microbial infection may be caused by at least one of a Gram-positive bacteria, a Gram negative bacteria, and fungus. The Gram-positive bacteria and the Gram negative bacteria can include at least one of *S. aureus, S. mutans, E. coli, N. meningitides,* and *Sa. Typhimurium*. The fungus species can include at least one of *C. albicans, C. parasilosus, P. chrysoginum, C. neoformasn, A. fumigatus* and *Fusarium* sp.

The trithiocarbonate derivative compound or pharmaceutical compositions thereof can be administered to a subject by any suitable route for treating or inhibiting bacterial and/or fungal infections. Parenteral, otic, ophthalmic, nasal, inhalable, buccal, sublingual, enteral, topical, oral, peroral, and injectable dosage forms are particularly useful. Particular dosage forms include solid or liquid dosage forms. Exemplary suitable dosage forms include tablet, capsule, pill, caplet, troche, sache, solution, suspension, dispersion, vial, bag, bottle, injectable liquid, i.v. (intravenous), i.m. (intramuscular) or i.p. (intraperitoneal) administrable liquid and other such dosage forms known to the artisan of ordinary skill in the pharmaceutical sciences.

The amount of trithiocarbonate derivative compound incorporated in a dose can be selected according to the examples provided herein and/or according to known principles of pharmacy. An effective amount or therapeutically effective amount of the trithiocarbonate derivative is specifically contemplated. A therapeutically effective amount is the amount or quantity of active ingredient which is enough for the required or desired therapeutic response, or in other words, the amount, which is sufficient to elicit an appreciable biological response when administered to a patient. The appreciable biological response, i.e., anti-microbial activities, can occur as a result of administration of single or multiple doses of an active substance. A dose may comprise one or more dosage forms. It will be understood that the specific dose level for any patient will depend upon a variety of factors including the indication being treated, severity of the indication, patient health, age, gender, weight, diet, pharmacological response, the specific dosage form employed, and other such factors.

The present teachings will be understood more readily by reference to the following examples, which are provided by way of illustration.

EXAMPLE 1

Synthesis of diethyl 2,2'-(thiocarbonylbis(sulfanediyl))diacetate (4)

A mixture of ethyl cyanoacetate 1 (0.1 mol), $CS_2$ 2 (0.2 mol) and ethyl 2-chloroacetate 3 (0.2 mol) was added to DMF (35 mL), followed by addition of anhydrous $K_2CO_3$ (30 g). The resulting mixture was stirred vigorously overnight at room temperature. The mixture reaction was cooled in an ice bath and the solid product was precipitated by addition of $H_2O$, collected by filtration, washed with $H_2O$, and dried. The crude product was added into cooled ethanol to afford compound 4 as crystal and then compound 5 was separated in a yield of 20%; m. p. 93° C. The compound 4 has following characteristics: Yield: 50%; m. p. 40° C.; IR (KBr, cm$^{-1}$) v=2978, 2930, 1732, 1475, 1367, 1300, 1202, 1155, 1095, 1069; 1H-NMR (500 MHz, CDCl13)=1.23 (t, J=7, 3H, —CH3), 4.14 (s, 2H, S—CH2-CO), 4.16 (q, 2H, J=7 Hz, —O—CH2-); 13C-NMR (125 MHz, CDCl$_3$)=14.0, 38.9, 62.1, 167.0, 220.2; MS m/z: 283.0 [M+H]$^+$, 267.1, 239.1, 207.0; Elemental Analysis: C, 38.28; H, 5.00; S, 34.06, Found: C, 38.31; H, 5.12; S, 33.97. The structural formula of Compound 4 is provided below.

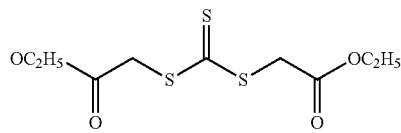 [SMILES: CCOC(=O)CSC(=S)SCC(=O)OCC]

Compound 4

The single-crystal X-ray diffraction of compound 4 was obtained as single crystals by slow evaporation from ethanol solution of the pure compound at room temperature. Data were collected on a Bruker APEX-II D8 Venture area diffractometer, equipped with graphite monochromatic CuKα radiation, λ=1.54178 Å at 293 (2) K. Cell refinement and data reduction were carried out by Bruker SAINT. SHELXT (Sheldrick 1997; Sheldrick 2008) was used to solve structure. The final refinement was carried out by full-matrix least-squares techniques with anisotropic thermal data for non-hydrogen atoms on F. CCDC 1522608 contains the supplementary crystallographic data for this compound can be obtained free of charge from the Cambridge Crystallographic Data Centre via www.ccdc.cam.ac.uk/data_request/cif.

Figure 2:
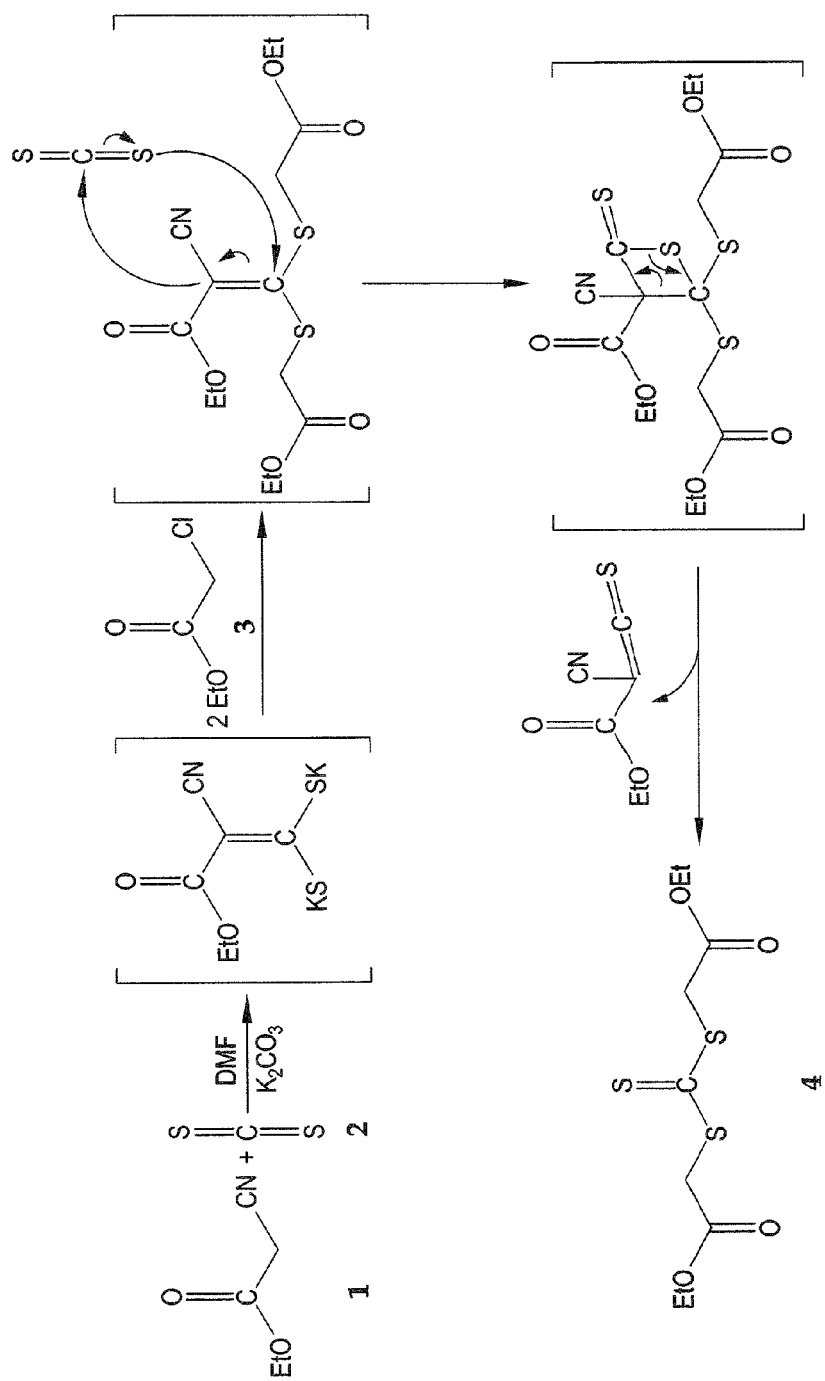
FIG. 2 shows a possible mechanism for formation of 2,2'-(thiocarbonylbis(sulfanediyl))diacetate compound.

As shown on FIG. 1, the reaction of ethyl cyanoacetate 1, carbon disulfide ($CS_2$) 2 and ethyl 2-chloroacetate 3 was successfully carried out affording 50% of trithiocarbonate 4 in addition to 20% of thiophene derivative 5. The reaction was carried out in the presence of anhydrous $K_2CO_3$ as base in DMF at room temperature. A plausible mechanism proposed to rationalize the formation of trithiocarbonate 4 is depicted in FIG. 2.

Figure 3:
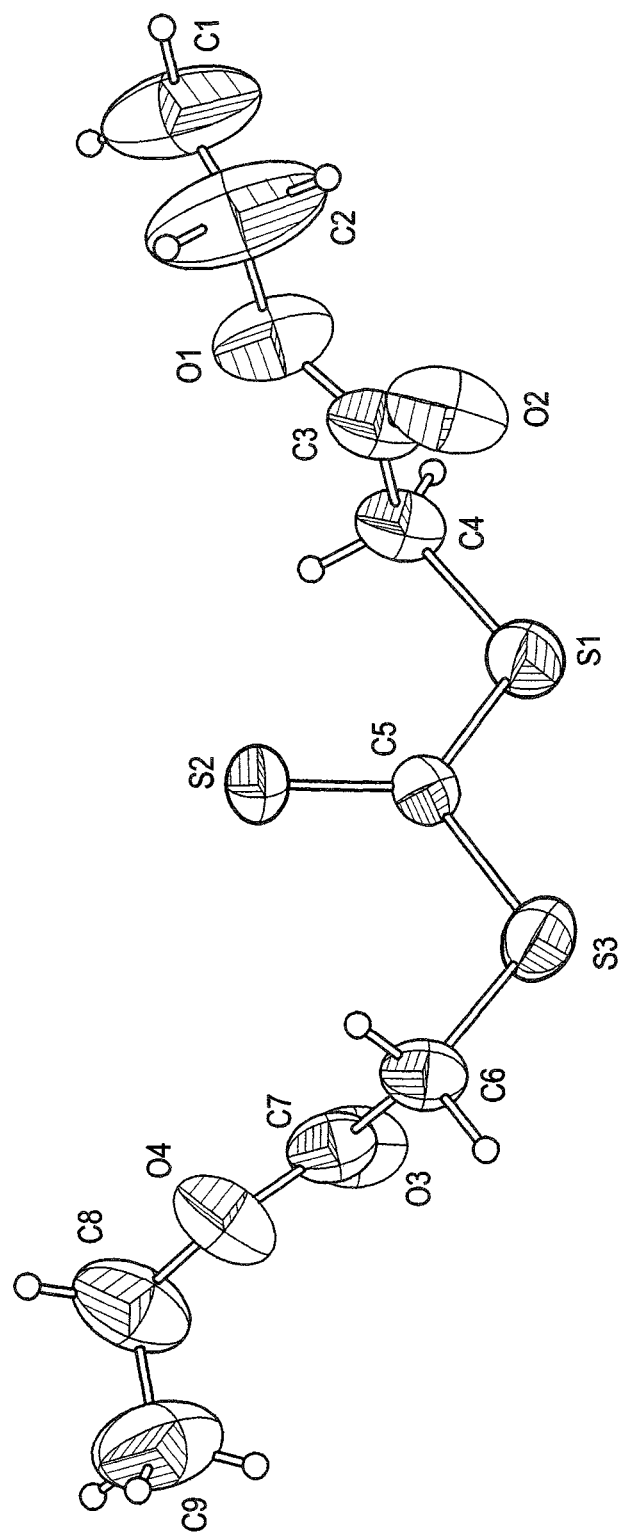
FIG. 3 shows an ORTEP diagram of the 2,2'-(thiocarbonylbis(sulfanediyl))diacetate compound synthesized by the present method, with displacement ellipsoids plotted at the 40% probability level for non-H atoms.
Figure 4:
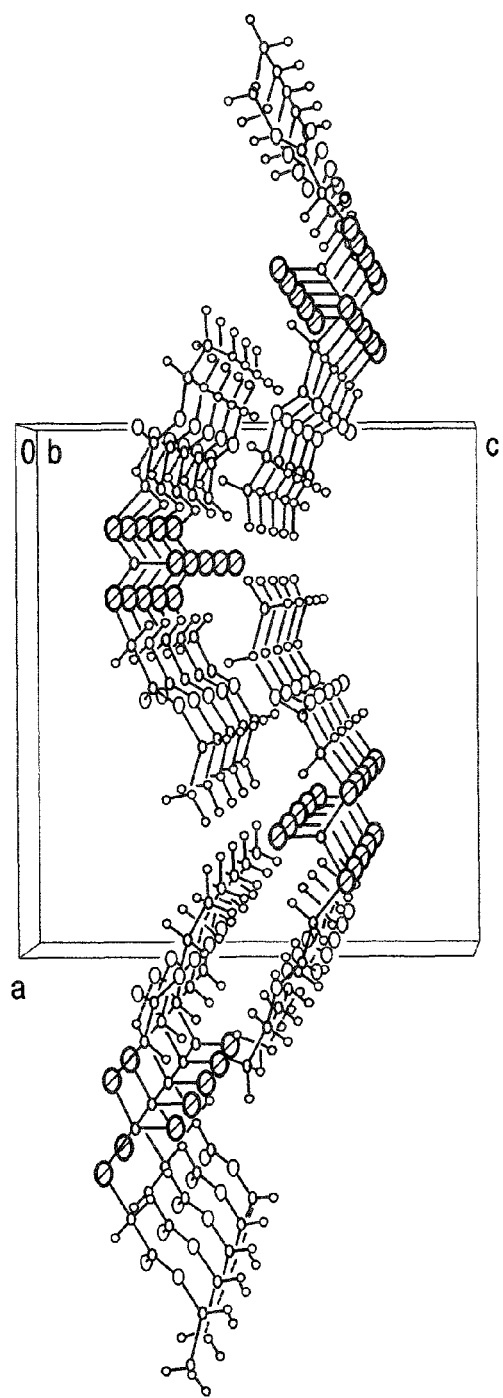
FIG. 4 shows molecular packing of the 2,2'-(thiocarbonylbis(sulfanediyl))diacetate compound viewed hydrogen bonds which are drawn as dashed lines along the b-axis.

The structure of the synthesized compound 4 was elucidated by using IR, $^1$H-NMR, $^{13}$C-NMR, HRMS and X-ray single crystallography. The IR spectrum of this compound displayed a characteristic absorption of the carbonyl and thiocarbonyl groups at υ 1732 and 1155 cm$^4$ respectively. The $^1$H-NMR and $^{13}$C-NMR spectra showed the symmetric pattern of the compound 4. The $^1$H-NMR spectrum exhibited triplet signal at δ 1.23 ppm with coupling constants J=7 Hz integrated for the protons assigned for methyl group (—OCH$_2$CH$_3$) and quartet signal at δ 4.16 ppm with coupling constants J=7 Hz integrated for the protons assigned for methylene group of ester functional group (—OCH$_2$CH$_3$) while the signal of protons assigned for the other methylene group (—S—CH$_2$CO—) is appeared as a singlet at δ 4.14 ppm. In the $^{13}$C-NMR spectrum, the peaks appeared at δ 14.0, 38.9 and 62.1 ppm were attributed to (—OCH$_2$CH$_3$), (—S—CH$_2$CO—) and (—OCH$_2$CH$_3$) respectively. The carbonyl group peak appeared at δ 167.0 ppm, while the peak of thiocarbonyl downshifted and appeared at δ 220.2 ppm. The x-ray single diffraction analysis clearly elucidated the molecular structure of compound 4. The crystallographic data and refinement information of this compound are summarized in Table 1. The selected bond lengths and bond angles are listed in Table 2. The asymmetric unit is shown in FIG. 3. All of the bond lengths and angles are in normal ranges. In the crystal packing, as show in in FIG. 4, molecules are linked via three non-classical intermolecular hydrogen bonds (Table 3).

TABLE 1

Experimental Data

Crystal data

| | |
|---|---|
| Chemical formula | $C_9H_{14}O_4S_3$ |
| Mr | 282.38 |
| Crystal system, space group | Monoclinic, $P2_1/c$ |
| Temperature (K) | 293 |
| a, b, c (Å) | 15.1354 (7), 4.8723 (2), 18.6434 (8) |
| β(°) | 91.866 (3) |
| V (Å3) | 1374.11 (10) |
| Z | 4 |
| Radiation type | Cu Kα |
| μ (mm$^{-1}$) | 4.93 |
| Crystal size (mm) | 0.37 × 0.19 × 0.12 |

Data collection

| | |
|---|---|
| Diffractometer | Bruker APEX-II D8 venture diffractometer |
| Absorption correction | Multi-scan SADABS Bruker 2014 |
| Tmin, Tmax | 0.266, 0.584 |
| No. of measured, independent and observed [I > 2σ(I)] reflections | 12063, 2196, 1348 |
| $R_{int}$ | 0.060 |

Refinement

| | |
|---|---|
| R[F$^2$ > 2σ(F$^2$)], wR(F$^2$), S | 0.077, 0.243, 1.03 |
| No. of reflections | 2196 |
| No. of parameters | 147 |
| No. of restraints | 2 |
| H-atom treatment | H atoms treated by a mixture of independent and constrained refinement |
| $Δρ_{max}$, $Δρ_{min}$ (e Å$^{-3}$) | 0.47, −0.36 |

TABLE 2

Selected Geometric Paramerters (Å, °)

| Bond | (Å, °) | Bond | (Å, °) |
|---|---|---|---|
| S1—C4 | 1.788 (5) | O1—C3 | 1.308 (9) |
| S1—C5 | 1.729 (5) | O2—C3 | 1.198 (8) |
| S2—C5 | 1.617 (4) | O3—C7 | 1.213 (8) |
| S3—C5 | 1.740 (5) | O4—C7 | 1.313 (9) |
| S3—C6 | 1.784 (5) | O4—C8 | 1.486 (11) |
| O1—C2 | 1.450 (12) | | |
| C4—S1—O5 | 103.6 (2) | S1—O5—S2 | 126.5 (3) |
| C5 S3—C6 | 103.1 (2) | S1—O5—S3 | 108.1 (2) |
| C2—O1—C3 | 116.6 (7) | S2—C5—S3 | 125.5 (3) |
| C7—O4—C8 | 118.5 (6) | S3—C6—C7 | 114.4 (4) |
| O1—C2—C1 | 117.2 (10) | O3—C7—O4 | 124.8 (6) |
| O1—C3—O2 | 124.4 (6) | O3—C7—C6 | 124.6 (6) |
| O1—C3—C4 | 108.9 (5) | O4—C7—C6 | 110.6 (5) |
| O2—C3—C4 | 126.6 (6) | O4—C8—C9 | 111.7 (9) |
| S1—C4—C3 | 113.2 (4) | | |

TABLE 3

Hydrogen-Bond Geometry (Å, °)

| D—H...A | D—H | H...A | D...A | D—H...A |
|---|---|---|---|---|
| C4—H4A...O2i | 0.9900 | 2.4600 | 3.319 (7) | 145.00 |
| C6—H6A...O3ii | 0.9900 | 2.5800 | 3.353 (7) | 135.00 |
| C6—H6A...O3iii | 0.9900 | 2.6000 | 3.260 (8) | 124.00 |

Symmetry codes: (i) x, y − 1, z; (ii) x, y + 1, z; (iii) −x + 1, y + 1/2, −z + 3/2.

EXAMPLE 2

In Vitro Antimicrobial Activity

To evaluate antimicrobial activity of the compound 4, synthesized in our laboratory as novel anti-bacterial and anti-fungal agents, the inhibition zone diameter (mm) and the minimal inhibitory concentration were determined according to (Andrews 2001; Hudzicki 2009). The test carried out on several clinical microorganisms included Gram positive bacteria (*Staphylococcus aureus* ATCC and *Streptococcus mutans* ATCC 35668), Gram negative bacteria (*Escherichia coli* ATCC 25922, *Salmonella typhimurium* ATCC 14028 and *Neisseria meningitides* ATCC 1302); yeasts (Candid *albicans* ATCC 60193, *Cryptococcus neoformans* Wild strain and *Candida parapsilosus* ATCC 22019) and molds (*Aspergillus fumigatus* AUMC 8794, *Penicillum chrysogenum* AUMC 9476 and *Fusarium* sp.)

The clinical microorganisms were cultivated at least three times on suitable culture medium and incubating conditions before susceptibility test. The concentration of microbial inoculation suspensions in sterile sodium chloride solution (0.89%) were adjusted to 0.65 at 620 nm by spectrophotometer. In the first stage, 150 mg of compound 4 were dissolved in 2000 μL of DMSO then 40 μL of solution added on sterile filter disk (6 mm) to obtain 3 mg per disk. To prepare a soluble water form of compound 4, 150 mg of compound 4 treated with sodium ethoxide were dissolved with 2000 μL of sterile distilled water then 40 L of solution was added on the filter disk (3 mg/disk). DMSO- and water-soluble forms of compound 4 were investigated by disk diffusion assay to determine the inhibition zone (mm) resulted from 3 mg of the compound per disk.

After that, the disks were dried at 25° C. under sterile conditions by safety biological cabinet. A Mueller-Hinton agar (MHA) (Scharlau Microbiogy, Spain) and a potato dextrose agar (PDA) (Scharlau, Spain) were used to perform antibacterial and antifungal test respectively. The media were prepared according to manufacturer's guidelines. To prepare one liter of MHA and one liter of PDA, 21 grams of MHA and 39 grams of PDA were dissolved in one liter of sterile distilled water, followed by sterilization at 121° C. for 15 minutes by an autoclave (HL-321, Taiwan). The sterilized media were poured in sterile plastic Petri dishes at 50° C. The plates were allowed to let the medium solidify at room temperature. 0.1 ml of microbial inoculation suspensions were spread on dried surface of medium and were kept at 25° C. for 5-10 minutes. The compound 4 and standard antimicrobial drugs discs (Table 1) were dispensed on the surface of inoculated media. The tested bacteria and fungi were incubated at 37±1° C. for 19-22 hours and at 25±1 for 48-72 hours respectively. After the incubation, the diameter of inhibition zone (millimeter) resulting from the biological activity of compound were recorded.

The minimal inhibitory concentration (MIC) of compound 4 (water-soluble form) was determined by a microdilution assay, using Mueller-Hinton broth (for bacteria) and Potato dextrose broth (for fungi). The compound 4 was dissolved in sterile culture broth (2 mg/mL). Two fold serial dilutions were carried out to obtain concentrations ranging from 2 to 0.008 mg/mL. 95 μL of each dilution were added in 96-well plates, then each well was inoculated with 5 μL of inoculation microbial suspension (5×10$^8$ colony form unit (CFU)/ml). The plates were incubated at suitable conditions according to tested microorganism. After the incubation, the microbial growth was detected in the wells by p-iodonitrotetrazolium violet (Sigma, USA) reagent. Each well received 20 μL of the reagent (0.5 mg/ml) and was then incubated at 37±1° C. for 30 min. A violet color indicated microbial growth in the well. The minimal inhibitory concentration (mg/ml) of the compound 4 was estimated as the lowest concentration that inhibited microbial growth.

EXAMPLE 3

In Vitro, Anti-Cancer Test

Biological activity of compound 4 (water soluble form) as anticancer in human breast cancer was evaluated according to (Kumar et al. 2014). Roswell Park Memorial Institute (RPMI)-1640 medium (Sigma, USA) were prepared according to manufacturer's guidelines and supplemented fetal bovine serum (10%). To avoid a microbial contamination, a streptomycin and penicillin were added to RPMI-1640. Several concentrations ranging from 4 to 0.008 mg/mL of compound 4 were tested.

EXAMPLE 4

In Vivo, Antifungal Activity

To confirm that the water soluble form of the compound 4 has a biological activity as a novel antimicrobial agent, effectiveness of the compound 4 as a drug to treat candidemia in mice was investigated. The experiment was performed in Experimental Animal Care Center (EACC), College of Pharmacy, King Saud University, Riyadh. Fifty Albino male mice, weighing nearly 30±2 gram were used. The mice were arranged in five groups, each including ten mice caged together, given water, and feed ad libitum. Negative control and control group were infected intravenously with 0.2 ml of C. albicans suspension ($10^6$ CFU/mouse) and 0.2 ml of sterile normal saline (0.89% Nacl) respectively. The group treated with standard drug (fluconazole) was infected intravenously with 0.2 ml of C. albicans suspension ($10^6$ CFU/mouse) and treated (orally) by 12 mg/kg of fluconazole (loading dose) on the first day followed by 6 mg/ml for 2 weeks. The group treated with the investigated compound 4 was infected intravenously with C. albicans at $10^6$ CFU/mouse (0.2 ml) and treated (orally) by 12 mg/kg of the compound 4 (loading dose) on the first day followed by 6 mg/ml for 2 weeks. To study the biological effects of compound 4, a fifth group was designed. In this group the mice were treated intravenously (I. V) with 12 mg/kg of the compound 4 on the first day followed by 6 mg/ml for 2 weeks. All doses of the standard drug and compound 4 were given twice daily.

The effectiveness of the previous treatments on some biological concepts were evaluated. The biological parameters included daily body weight (gm), mortality (%), food consumption (g/day/mouse), water consumption (ml/day/mouse), serum glutamic oxaloacetic transaminase [SGOT (AST) (U/L)], serum glutamic-pyruvic transaminase [SGPT (ALT)(U/L)], alkaline phosphatase (U/L), gamma-glutamyl transferase (GGT) (U/L), bilirubin (mg/dl)], cholesterol (mg/dl), triglycerides (mg/dl), high-density lipoprotein (HDL) (mg/dl), very-low-density lipoprotein (VLDL) (mg/dl), low-density lipoprotein (LDL) (mg/dl), lactate dehydrogenase (LDH) (U/L), glucose (mg/dl), total protein (mg/dl), malondialdehyde (MDA) (nmol/g), nonprotein sulfyhydryl (NP-SH) (nmol/g). Addition hematologic constituents including white blood cells (WBC) (cell/mm$^3$), red blood cells (RBC) ($10^6$/mm$^3$), hemoglobin (HGB) (g/dL), HCT, Platelets (PLT) ($10^3$/mm$^3$), mean corpuscular volume (MCV) (fL), mean corpuscular hemoglobin (MCH) (pg), mean corpuscular hemoglobin concentration (MCHC) (g/dL), neutrophils (%), lymphocytes (%), eosinophils (%) and monocytes (%)] were evaluated (Classics Lowry et al. 1951; Utley et al. 1967; Sedlak et al. 1968). SGOT (AST), SGPT (ALT), ALP, GGT, bilirubin LDH and total protein were estimated using Reflotron Plus Analyzer and Roche kits (Roche Diagnostics GmbH, Mannheim Germany) and United diagnostic kits assay. Hematological tests were performed by Mindray BC-2800VET auto Hematology Analyzer.

The results of the tests on biological activity of compound 4 as antimicrobial and anticancer agent indicated that the compound had no biological activity as anticancer against MCF-7 human breast cancer cell lines. The data further indicated, as shown in Table 4, that compound 4 had biological activity as antimicrobial agents, i.e., antibacterial and antifungal agents, against all pathogenic microorganisms that were tested. Both the water- and DMSO soluble forms were effective against the microorganisms.

All tested fungi (C. albicans, Cr. neoformans, A. niger, P. chrysogenum, Fusairum sp. except C. parapsilosus) showed significantly (P<0.05) susceptible to the compound. In A. fumigatus mold, the inhibition resulted by the compound was significant (P<0.05) more than resulted in standard antifungal drugs (Cycloheximide, Canesten and Caspofungin). A. fumigatus used in this work, is one of strains that isolated from human suffered aspergillosis disease in Ryiad city, KSA in our previous study (Niazi et al. 2014). A. fumigatus mold, which lives outdoors and indoors, is considered a real risk in individuals with an immunodeficiency or lung illnesses (O'Gorman et al. 2009). The compound 4 as antifungal agent against Cr. neoformans showed high biological activity, the inhibition zone and minimal inhibitory concentration reached 30 mm and 0.03125 mg/ml, respectively. Cr. neoformans strain used in this study showed resistance to caspofungin. It was previously confirmed that caspofungin have limited activity against Cr. neoformans that causes several diseases, e.g., cryptococcosis (Tripathi et al. 2012). The results in Table 4 refer to efficiency of the compound to inhibit both pathogenic yeasts and molds, especially its effectiveness to inhibit cycloheximide, canesten and caspofungin resistant C. parasilosus. Both gram positive and negative bacteria, used in this research, are inhibited by the compound 4 (Table 4). The biological activity against S. mutans (It has a major role in tooth decay) and N. meningitides (It can cause meningitis) was very good.

The present inventive method and results demonstrates that compound 4 has biological activity as novel broad-spectrum antimicrobial agent. To confirm and support the results obtained from in vitro study, the animal experiment was carried out. In this stage, the role of the water-soluble compound 4 was evaluated to treat the mice infected with C. albicans (candidemia).

In the experiments, Co1, Co2, FluCal, ComCal and Comp were used to test mice treated with sterile normal saline, infected with C. albicans, treated with Diflucan (fluconazole) (Pfizer Inc. New York, N.Y., U.S.A), treated with the compound 4 and injected only with the chemical, respectively. Results are provided in the tables that follow. In Table 5, a percentage change refers to the change in weight of treated groups compared with control group (Co1). At the end of the 15$^{th}$ day, the data showed that the percentage change of groups treated with fluconazole and compound 4 were convergent changes, whereas the percentage change of group infected with C. albicans (Co2) was the highest. The C. albicans caused dramatic increases in daily mortality compared with control group. The results demonstrated that the compound 4 at dose of 800 mg as the loading dose, followed by 400 mg/d for 2 week reduced the mortality (%) caused by C. albicans. The results confirmed that the compound 4 have nearly similar effects to fluconazole (Table 8). The mortality in the group treated only with the compound 4 was close to the control group. The effectiveness of the previous treatments on serum marker enzymes of the mice were evaluated and represented in Table 9. Activity of serum marker enzymes (SGOT, SGPT, alkaline phosphatase, GGT and bilirubin) significantly ($p<0.001$) increased in group infected with C. albicans (negative control) comparing with control group. Activity of serum marker enzymes significantly ($p<0.001$) increased in group infected with C. albicans and treated with fluconazole compared with the group infected with C. albicans. The results obtained from the group that was treated with the compound 4 as anti-C. albicans showed significant ($p<0.001$) increase except for activity of SGOT. In group injected only with compound 4 there was a significant ($p<0.01$) decreasing in activity of SGOT compared with control group.

Table 10 shows the concentration of serum lipoproteins (mg/dl) in the tested mice. The data confirmed that C. albicans lead to significant ($p<0.001$) rise in cholesterol, triglycerides, VLDL and LDL level whereas it caused significant ($p<0.001$) decrease in HDL level. These effects resulted by C. albicans significantly ($p<0.001$) decreased in groups that treated with the compound 4 and fluconazole. The control treated only with the compound 4 showed significant ($p<0.001$) decrease in cholesterol, triglycerides, VLDL and LDL level and non-significant increase in HDL comparing with the control group. The data, shown in Table 11, revealed that C. albicans caused significant ($p<0.001$) increase in glucose and LDH and caused significant ($p<0.001$) decrease in total protein level in serum blood of mice comparing with the control group. The effects of C. albicans (Table 11) were significantly decreased by compound 4 and fluconazole ($p<0.01$, $p<0.001$ respectively). The glucose and total protein level in serum blood of mice injected only with compound 4 significantly decreased ($p<0.01$) and increased ($p<0.05$) respectively, while no significant changes were seen in in LDH level. The MDA, total protein and NP-SH in liver tissue of the mice were estimated in the previous treatments (Table 12). There were significant ($P<0.001$) differences between control group and negative control group infected with C. albicans. The compound 4 and fluconazole played a nearly identical role in reducing the biological effects that resulted from C. albicans (Table 12). Table 13 showed that all hematologic parameters in the mice decreased in the group infected with C. albicans compared with injecting with sterile normal saline. Lymphocytes excluded from the results in Table 13 showed significant ($p<0.001$) increase. Compound 4 and fluconazole decreased the hematologic changes resulting from C. albicans except for monocytes (%). The data obtained from in vivo tests confirmed that compound 4 significantly reduces the activity of aspartate aminotransferase (AST), cholesterol, triglycerides, VLDL, LDL, and glucose, MDA, WBC and lymphocytes in serum of mice. Also, it significantly increases other hematologic parameters, total protein of serum and total protein of liver tissue.

The present results obtained from in vitro and in vivo experiments suggest that compound 4 can be a novel antibacterial and antifungal drug. Antimicrobial agents can be grouped, based on their chemical structures, as aminoglycosides, anasamacrolides, beta-lactams, chloramphenicol and analagues, Lincosamides, macrolides, nucleosides, puromycin, peptides, phenazines, polyenes, polyethers and tetracyclines. Recent scientific research focuses on the function and inhibition of fungal β-carbonic anhydrases and bacterial carbonic anhydrases (α-, β-, and/or γ-carbonic anhydrases familie) as novel antifungal and antibacterial targets. Based on its chemical structure, compound 4 is belongs to the trithiocarbonate class. This class is considered as strong inhibitor of carbonic anhydrases.

The biological activity of soluble water compound 4 as antimicrobial agents against some medical microorganisms is provided in Table 4.

TABLE 4

| | | Compound 4 (4 mg/disk) | | Inhibition zone diameter (mm) of standard antimicrobial agents | | | | | |
|---|---|---|---|---|---|---|---|---|---|
| | | | | Standard antibacterial agent | | | Standard antifungal agent | | |
| | Micro-organisms | Inhibition zone diameter (mm) | Minimal inhibitory concentration (mg/ml) | Tobramycin (10 µg/desk) | Chloramphenicol (30 µg/disk) | Fusidic acid (10 µg/disk) | Cyclo-heximide (30 µg/disk) | Canesten (10 µg/disk) | Caspofungin (10 µg/disk) |
| Gram positive bacteria | S. aureus | 10.6 ± 0.5 F* | 2 | 14 | 30 | 23 | N.T | N.T | N.T |
| | S. mutans | 20 ± 1 D | 0.0625 | 35 | 20 | 10 | N.T | N.T | N.T |
| Gram negative bacteria | E. coli | 11.6 ± 0.5 E | 1 | 20 | 40 | 0 | N.T | N.T | N.T |
| | N. meningitides | 22.6 ± 0.5 C | 0.0625 | 21 | 34 | 20 | N.T | N.T | N.T |
| | Sa. typhimurium | 8.6 ± 0.5 F | 2 | 14 | 30 | 0 | N.T | N.T | N.T |
| Yeasts | C. albicans | 20 ± 1 D | 0.0625 | N.T | N.T | N.T | 0 | 26 | 20 |
| | C. neoformasn | 30 ± 1 B | 0.03125 | N.T | N.T | N.T | 32 | 25 | 0 |
| | C. parasilosus | 13 ± 1 E | 0.05 | N.T | N.T | N.T | 0 | 0 | 0 |
| Molds | P. chrysoginum | 30.3 ± .5 B | 0.03125 | N.T | N.T | N.T | 23 | 30 | 0 |
| | A. fumigatus | 34.6 ± 0.5 A | 0.03125 | N.T | N.T | N.T | 22 | 23 | 20 |
| | Fusarium sp. | 30 ± 1 B | 0.03125 | N.T | N.T | N.T | 30 | 15 | 0 |

*The mean of inhibition zone diameter (mm) ± Standard division. In the same column, the means with different letters are significant at $P < 0.05$.

The daily body weight (gm) of Albino male mice infected with C. albicans and treated with the fluconazole and the compound 4 for 15 days is provided in Table 5.

TABLE 5

| Days↓ | Co1* | Co2 | FluCal | Comp. | CompCal. |
|---|---|---|---|---|---|
| 0 | 19.20 ± 0.35** | 19.9 ± 0.43 | 19.70 ± 0.47 | 20.20 ± 0.38 | 21.00 ± 0.36 |
| 1 | 20.10 ± 0.31 4.68↑** | 19.9 ± 0.37 0.00 | 19.80 ± 0.35 0.50 | 20.30 ± 0.36 0.49 | 21.50 ± 0.26 2.38 |
| 2 | 21.1 ± 0.31 9.89 | 20.8 ± 0.38 4.52 | 21.80 ± 0.24 10.65 | 22.10 ± 0.23 9.40 | 22.00 ± 0.25 4.76 |
| 3 | 21.7 ± 0.21 13.02 | 21.7 ± 0.3 9.04 | 22.30 ± 0.21 13.19 | 23.60 ± 0.33 16.83 | 22.3 ± 0.21 6.19 |
| 4 | 22.2 ± 0.20 15.62 | 22.22 ± 0.27 11.66 | 22.40 ± 0.22 13.70 | 24.20 ± 0.20 19.80 | 22.90 ± 0.27 9.04 |
| 5 | 22.3 ± 0.21 16.14 | 24.00 ± 0.26 20.60 | 23.90 ± 0.31 21.31 | 24.90 ± 0.23 23.26 | 23.55 ± 0.37 12.16 |
| 6 | 23.2 ± 0.24 20.83 | 25.37 ± 0.26 27.51 | 24.00 ± 0.29 21.82 | 25.70 ± 0.21 27.22 | 24.22 ± 0.32 15.34 |
| 7 | 23.9 ± 0.23 24.47 | 25.12 ± 0.29 26.25 | 24.22 ± 0.22 22.95 | 26.20 ± 0.24 29.70 | 24.66 ± 0.23 17.46 |
| 8 | 24.2 ± 0.24 26.04 | 26.12 ± 0.29 31.28 | 24.44 ± 0.24 24.08 | 26.70 ± 0.26 32.17 | 24.87 ± 0.29 18.45 |
| 9 | 24.9 ± 0.23 29.68 | 27.00 ± 0.48 35.67 | 24.50 ± 0.18 24.36 | 26.80 ± 0.29 32.67 | 25.25 ± 0.25 20.23 |
| 10 | 25.00 ± 0.22 30.20 | 27.42 ± 0.48 37.83 | 24.87 ± 0.29 26.29 | 27.00 ± 0.27 33.66 | 25.37 ± 0.26 20.83 |
| 11 | 25.70 ± 0.22 33.85 | 27.85 ± 0.40 39.98 | 25.25 ± 0.25 28.17 | 27.40 ± 0.35 35.64 | 26.14 ± 0.26 24.48 |
| 12 | 26.3 ± 0.27 36.97 | 27.83 ± 0.40 39.86 | 25.37 ± 0.26 −28.80 | 27.66 ± 0.28 36.96 | 26.28 ± 0.28 25.17 |
| 13 | 26.7 ± 0.38 39.06 | 29.50 ± 0.42 48.24 | 26.00 ± 0.30 31.97 | 27.77 ± 0.27 35.51 | 27.28 ± 0.28 29.93 |
| 14 | 27.55 ± 0.29 43.51 | 29.16 ± 0.47 46.56 | 26.28 ± 0.28 33.43 | 28.00 ± 0.37 38.61 | 28.33 ± 0.49 34.92 |
| 15 | 28.00 ± 0.40 45.83 | 30.20 ± 0.73 51.78 | 26.71 ± 0.28 35.60 | 28.62 ± 0.41 41.70 | 28.66 ± 0.33 36.50 |

*Co1 = control group treated with sterile normal saline, Co2 = negative control infected with *C. albicans*, Flucal = group infected with *C. albicans* and treated with fluconazole, Comp = group treated with the compound 4 and CompCal = group infected with *C. albicans* and treated with the compound 4.
**Mean ± SE,
***% change in daily body weight (gm) comparing with control group.

Table 6 provides the food consumption (g/day/mouse) of Albino male mice infected with *C. albicans* and treated with the fluconazole and the compound 4. Both fluconazaole and the compound 4 had nearly identical effects on food and water consumption. The investigated compound 4 had no negative side effects on food and water consumption comparing with control group (Tables 6 and 7).

TABLE 6

| | Days | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Co1* | 4.5** | 4.6 | 4.6 | 4.7 | 4.8 | 5.0 | 5.2 | 5.5 | 5.7 | 5.7 | 5.9 | 5.9 | 6.0 | 6.1 | 6.2 |
| Co2 | 4.1 | 4.1 | 4.3 | 4.2 | 4.5 | 4.6 | 4.8 | 4.8 | 4.5 | 4.8 | 5.5 | 5.6 | 5.5 | 5.8 | 6.0 |
| FluCal | 4.3 | 4.3 | 4.5 | 4.6 | 4.6 | 4.7 | 5.0 | 5.1 | 4.7 | 5.00 | 5.1 | 5.62 | 5.2 | 5.2 | 5.5 |
| Comp. | 4.2 | 4.5 | 4.4 | 4.5 | 4.6 | 4.6 | 4.8 | 4.9 | 4.9 | 5.1 | 5.2 | 6.0 | 6.0 | 6.1 | 6.1 |
| CompCal. | 4.5 | 4.6 | 4.7 | 4.9 | 4.00 | 4.2 | 4.2 | 4.3 | 4.5 | 4.5 | 4.7 | 5.0 | 5.14 | 5.3 | 5.5 |

*Co1 = control group treated with sterile normal saline, Co2 = negative control infected with *C. albicans*, Flucal = group infected with *C. albicans* and treated with fluconazole, Comp = group treated with the compound 4 and CompCal = group infected with *C. albicans* and treated with the compound 4.
**Food consumption (g/day/mice).

Table 7 provides the water consumption (ml/day/mouse) of Albino male mice infected with *C. albicans* and treated with the fluconazole and the compound 4.

TABLE 7

| | Days | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Co1* | 5.1** | 5.1 | 5.2 | 5.3 | 5.3 | 5.4 | 5.4 | 5.6 | 5.8 | 5.7 | 5.8 | 5.8 | 5.9 | 6.1 | 6.2 |
| Co2 | 4.4 | 4.5 | 4.5 | 4.4 | 4.6 | 4.8 | 5.0 | 5.1 | 5.0 | 5.1 | 5.1 | 5.0 | 5.3 | 5.5 | 6.0 |

TABLE 7-continued

| | Days | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| FluCal | 4.8 | 4.8 | 4.9 | 5.0 | 5.2 | 5.2 | 5.1 | 5.2 | 5.2 | 5.3 | 5.3 | 5.5 | 5.4 | 5.4 | 5.7 |
| Comp. | 5.2 | 5.2 | 5.4 | 5.5 | 5.5 | 5.7 | 5.8 | 5.8 | 5.9 | 5.9 | 6.0 | 6.11 | 6.2 | 6.2 | 6.3 |
| CompCal. | 4.5 | 4.5 | 4.7 | 4.9 | 4.2 | 4.6 | 5.7 | 4.6 | 4.6 | 4.8 | 5.1 | 5.4 | 5.5 | 5.5 | 5.8 |

*Co1 = control group treated with sterile normal saline, Co2 = negative control infected with *C. albicans*, Flucal = group infected with *C. albicans* and treated with fluconazole, Comp = group treated with the compound 4 and CompCal = group infected with *C. albicans* and treated with the compound 4.
**Water consumption (g/day/mice).

Table 8 provides the daily mortality (%) in Albino male mice infected with *C. albicans* and treated with the fluconazole and the compound 4. The *C. albicans* caused dramatic increases in daily mortality compared with control group.

TABLE 8

| | Days | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Co1* | 0** | 0 | 0 | 0 | 0 | 0 | 0 | 0 | 0 | 0 | 0 | 0 | 0 | 10 | 10 |
| Co2 | 0 | 0 | 0 | 10 | 20 | 20 | 20 | 20 | 30 | 30 | 30 | 40 | 40 | 40 | 50 |
| FluCal | 0 | 0 | 0 | 0 | 0 | 0 | 10 | 10 | 20 | 20 | 20 | 20 | 30 | 30 | 30 |
| Comp. | 0 | 0 | 0 | 0 | 0 | 0 | 0 | 0 | 0 | 0 | 0 | 10 | 10 | 10 | 10 |
| CompCal. | 0 | 0 | 0 | 0 | 10 | 10 | 10 | 20 | 20 | 20 | 30 | 30 | 30 | 30 | 30 |

*Co1 = control group treated with sterile normal saline, Co2 = negative control infected with *C. albicans*, Flucal = group infected with *C. albicans* and treated with fluconazole, Comp = group treated with the compound 4 and CompCal = group infected with *C. albicans* and treated with the compound 4.
**Mortality (%).

The activity of serum marker enzymes of Albino male mice infected with *C. albicans* and treated with the fluconazole and compound 4 is provided on Table 9.

TABLE 9

| | SGOT(AST) U/L | | SGPT(ALT) U/L | | Alkaline phosphatase E(U/L) | | GGT (U/L) | | Bilirubin (mg/dl) | |
|---|---|---|---|---|---|---|---|---|---|---|
| | Mean ± SE | % Change | Mean ± SE | % Change | Mean ± SE | % Change | Mean ± SE | % Change | Mean ± SE | % Change |
| Co1* | 107.45 ± 2.71 | | 27.07 ± 0.53 | | 296.88 ± 4.35 | | 4.94 ± 0.14 | | 0.54 ± 0.01 | |
| Co2 | 204.8 ± 5.86 ***$a$ | 90.59↑ | 125.20 ± 7.45 ***$a$ | 362.37↑ | 414.80 ± 6.75 ***$a$ | 39.71↑ | 9.70 ± 0.29 ***$a$ | 9617↑ | 1.67 ± 0.04 ***$a$ | 209.46↑ |
| FluCal | 143.28 ± 2.88 ***$b$ | 30.03↓ | 50.48 ± 3.17 ***$b$ | 59.67↓ | 321.28 ± 6.91 ***$b$ | 22.54↓ | 5.60 ± 0.17 ***$b$ | 42.26↓ | 0.75 ± 0.03 ***$b$ | 55.13↓ |
| Comp. | 89.07 ± 3.82 ***$a$ | 17.10↓ | 28.67 ± 1.15$a$ | 5.89↑ | 286.62 ± 4.67$a$ | 3.45↓ | 4.40 ± 0.13$a$ | 11.10↓ | 0.57 ± 0.017$a$ | 6.04↑ |
| CompCal. | 169.33 ± 2.69 ***$b$ | 17.31↓ | 83.50 ± 2.35 ***$b$ | 33.30↓ | 354.66 ± 5.57 ***$b$ | 14.49↓ | 7.18 ± 0.20 ***$b$ | 25.94↓ | 1.15 ± 0.03 ***$b$ | 31.16↓ |

*Co1 = control group treated with sterile normal saline, Co2 = negative control infected with *C. albicans*, Flucal = group infected with *C. albicans* and treated with fluconazole, Comp = group treated with the compound 4 and CompCal = group infected with *C. albicans* and treated with the compound 4.
All values represent mean ± SEM.
***$p < 0.001$; Student's- t-test.
$a$As compared with control group.
$b$As compared with *C. albicans* group.

The serum lipoproteins of Albino male mice infected with *C. albicans* and treated with the fluconazole and the compound 4 is provided in Table 10.

TABLE 10

| Treatments | Cholesterol (mg/dl) Mean ± SE | % Change | Triglycerides (mg/dl) Mean ± SE | % Change | HDL (mg/dl) Mean ± SE | % Change | VLDL (mg/dl) Mean ± SE | % Change | LDL (mg/dl) Mean ± SE | % Change |
|---|---|---|---|---|---|---|---|---|---|---|
| Co1* | 98.17 ± 2.1 | | 85.3 ± 2.7 | | 39.0 ± 0.7 | | 17.0 ± 0.5 | | 42.0 ± 2.2 | |
| Co2 | 212.8 ± 6.0 ***a | 116.7↑ | 186.8 ± 6.0 ***a | 118.8↑ | 21.1 ± 0.9 ***a | 45.8↓ | 37.3 ± 1.21 ***a | 118.8↑ | 154.2 ± 5.7 ***a | 267.1↑ |
| FluCal | 134.8 ± 3.6 ***b | 36.6↓ | 105.1 ± 2.2 ***b | 4.37↓ | 29.8 ± 0.9 ***b | 41.1↑ | 21.0 ± 0.4 ***b | 43.7↓ | 83.9 ± 3.3 ***b | 45.5↓ |
| Comp. | 78.68 ± 3.2 ***a | 19.85↓ | 68.5 ± 1.6 ***a | 19.6↓ | 41.6 ± 2.1a | 6.42↑ | 13.7 ± 0.3 ***a | 19.6↓ | 23.3 ± 3.0 ***a | 44.35↓ |
| CompCal. | 159.8 ± 3.4 ***b | 24.8↓ | 134.8 ± 3.8 ***b | 27.8↓ | 26.9 ± 1.1 **b | 27.2↑ | 26.9 ± 0.7 ***b | 27.8↓ | 105.9 ± 4.6 ***b | 31.3↓ |

*Co1 = control group treated with sterile normal saline, Co2 = negative control infected with *C. albicans*, Flucal = group infected with *C. albicans* and treated with fluconazole, Comp = group treated with the compound 4 and CompCal = group infected with *C. albicans* and treated with the compound 4.
All values represent mean ± SEM.
**$p < 0.01$;
***$p < 0.001$; Student's- t-test.
$^a$As compared with control group.
$^b$As compared with *C. albicans* group.

The serum glucose, total protein and LDH of Albino male mice infected with *C. albicans* and treated with the fluconazole and the compound 4 is provided on Table 11.

TABLE 11

| Treatments | Glucose level (mg/dl) Mean ± SE | % Change | Total Protein (mg/dl) Mean ± SE | % Change | LDH Mean ± SE | % Change |
|---|---|---|---|---|---|---|
| Co1* | 113.95 ± 2.96 | | 7.11 ± 0.15 | | 158.84 ± 3.00 | |
| Co2 | 204.2 ± 7.58*a | 79.19↑ | 3.55 ± 0.08*a | 50.05↓ | 245.18 ± 5.12***a | 54.35↑ |
| FluCal | 143.85 ± 2.47*b | 29.55↓ | 5.64 ± 0.11*b | 58.79↑ | 184.92 ± 5.08***b | 24.57↓ |
| Comp. | 96.38 ± 3.62**a | 15.41↓ | 7.66 ± 0.18*a | 7.69↑ | 162.50 ± 1.84a | 2.29↑ |
| CompCal. | 166.83 ± 4.32b | 18.29↓ | 4.91 ± 0.09*b | 38.14↑ | 220.98 ± 3.96**b | 9.86↓ |

*Co1 = control group treated with sterile normal saline, Co2 = negative control infected with *C. albicans*, Flucal = group infected with *C. albicans* and treated with fluconazole, Comp = group treated with the compound 4 and CompCal = group infected with *C. albicans* and treated with the compound 4.
All values represent mean ± SEM.
**$p < 0.01$;
***$p < 0.001$; Student's- t-test.
$^a$As compared with control group.
$^b$As compared with *C. albicans* group.

The MDA, Total Protein and NP-SH in liver tissue of Albino male mice infected with *C. albicans* and treated with the fluconazole and the compound 4 is provided on Table 12.

TABLE 12

| Treatments | MDA (nmol/g) | Total Protein (g/l) | NP-SH (nmol/g) |
|---|---|---|---|
| Co1* | 1.24 ± 0.02 | 115.23 ± 1.80 | 5.70 ± 0.14 |
| Co2 | 6.36 ± 0.25*a | 65.14 ± 2.06*a | 1.61 ± 0.14***a |
| FluCal | 2.33 ± 0.07*b | 92.72 ± 1.54*b | 4.21 ± 0.18***b |
| Comp. | 0.94 ± 0.03*a | 129.04 ± 2.80a | 6.88 ± 0.22***a |
| CompCal. | 4.57 ± 0.25*b | 77.84 ± 2.37b | |

* Co1 = control group treated with sterile normal saline, Co2 = negative control infected with *C. albicans*, Flucal = group infected with *C. albicans* and treated with fluconazole, Comp = group treated with the compound 4 and CompCal = group infected with *C. albicans* and treated with the compound 4. All values represent mean ± SEM.
**$p < 0.01$;
***$p < 0.001$; Student's- t-test.
$^a$As compared with control group.
$^b$As compared with *C. albicans* group.

The hematological studies of Albino male mice infected with *C. albicans* and treated with the fluconazole and the compound 4 are provided in Table 13.

TABLE 13

|  | Co1* | Co2 | | FluCal | | Comp. | | CompCal. | |
| --- | --- | --- | --- | --- | --- | --- | --- | --- | --- |
| Treatments | Mean ± SE | Mean ± SE | % Change | Mean ± SE | % Change | Mean ± SE | % Change | Mean ± SE | % Change |
| WBC (Cell/mm$^3$) | 8582.2 ± 17.7 | 6513.6 ± 24.0 ***$^a$ | 24.1↓ | 8233.2 ± 83.7 ***$^b$ | 26.4↑ | 8795 ± 45.9 **$^a$ | 2.48↑ | 7540.8 ± 87.3 ***$^b$ | 15.9↑ |
| RBC (10$^6$/mm$^3$) | 8.14 ± 0.17 | 4.46 ± 0.19 ***$^a$ | 45.23↓ | 7.50 ± 0.23 ***$^b$ | 68.16↑ | 9.26 ± 0.1 **$^a$ | 13.72↑ | 6.16 ± 0.1 ***$^b$ | 38.2↑ |
| HGB (g/dL) | 11.9 ± 0.18 | 7.62 ± 0.16 ***$^a$ | 17.9↓ | 11.1 ± 0.18 ***$^b$ | 46.7↑ | 12.4 ± 0.18$^a$ | 3.4↑ | 9.8 ± 0.14 ***$^b$ | 28.6↑ |
| HCT | 42.48 ± 1.47 | 23.3 ± 1.54 ***$^a$ | 44.9↓ | 35.05 ± 1.5 ***$^b$ | 49.9↑ | 45.9 ± 1.51$^a$ | 8.2↑ | 31.3 ± 0.42 ***$^b$ | 33.8↑ |
| PLT (10$^3$/mm$^3$) | 618.0 ± 15.5 | 441.2 ± 24.7 ***$^a$ | 28.6↓ | 563.8 ± 17.4 **$^b$ | 27.8↑ | 670.7 ± 15.3 *$^a$ | 8.5↑ | 522.3 ± 10.1 *$^b$ | 18.3↑ |
| MCV (fL) | 75.84 ± 3.72 | 43.5 ± 2.5 ***$^a$ | 42.5↓ | 72.04 ± 2.6 ***$^b$ | 65.4↑ | 87.31 ± 1.74 *$^a$ | 15.1↑ | 53.7 ± 2.0 *$^b$ | 23.4↑ |
| MCH (pg) | 29.9 ± 0.97 | 21.2 ± 0.5 ***$^a$ | 28.9↓ | 28.2 ± 0.7 ***$^b$ | 32.6↑ | 39.0 ± 1.0 ***$^a$ | 30.4↑ | 26.3 ± 0.5 ***$^b$ | 23.6↑ |
| MCHC (g/dL) | 27.87 ± 0.94 | 19.3 ± 0.7 ***$^a$ | 30.6↓ | 24.3 ± 0.5 ***$^b$ | 25.9↑ | 32.6 ± 0.9 **$^a$ | 17.0↑ | 23.4 ± 1.0 *$^b$ | 21.1↑ |
| Neutrophils (%) | 28.88 ± 0.71 | 21.0 ± 0.4 ***$^a$ | 27.3↓ | 25.9 ± 0.5 ***$^b$ | 23.3↑ | 33.3 ± 1.1 **$^a$ | 15.3↑ | 24.1 ± 0.2 ***$^b$ | 15.0↑ |
| Lymphocytes (%) | 5.49 ± 0.10 | 8.8 ± 0.2 ***$^a$ | 60.7↑ | 6.2 ± 0.1 ***$^b$ | 29.2↓ | 4.8 ± 0.09 **$^a$ | 11.3↓ | 7.10 ± 0.07 ***$^b$ | 19.4↓ |
| Eosinophils (%) | 1.74 ± 0.04 | 0.96 ± 0.05 ***$^a$ | 44.8↓ | 1.61 ± 0.10 ***$^b$ | 68.3↑ | 2.38 ± 0.09 ***$^a$ | 36.7↑ | 1.30 ± 0.02 ***$^b$ | 36.1↑ |
| Monocytes (%) | 1.04 ± 0.02 | 0.96 ± 0.02 *$^a$ | 7.98↓ | 1.06 ± 0.02 *$^b$ | 11.16↑ | 1.15 ± 0.01 ***$^a$ | 10.7↑ | 0.88 ± 0.07$^b$ | 7.9↓ |

*Co1 = control group treated with sterile normal saline, Co2 = negative control infected with *C. albicans*, Flucal = group infected with *C. albicans* and treated with fluconazole, Comp = group treated with the compound 4 and CompCal = group infected with *C. albicans* and treated with the compound 4.
All values represent mean ± SEM.
**p < 0.01;
***p < 0.001; Student's- t-test.
$^a$As compared with control group.
$^b$As compared with *C. albicans* group.

As set forth above, the diethyl 2,2' (thiocarbonyl bis (sulfanediyl)) diacetate (compound 4) possesses broad spectrum antimicrobial activity as tested in vitro and in vivo.

It is to be understood that the present invention is not limited to the embodiments described above, but encompasses any and all embodiments within the scope of the following claims.

We claim:

1. A method for preparing a trithiocarbonate compound, comprising:
   mixing ethyl cyanoacetate, carbon disulfide and ethyl chloroacetate in an organic solvent to form a first reaction mixture;
   adding potassium carbonate into the first reaction mixture to form a second mixture;
   cooling the second mixture; and
   adding water to the second mixture to precipitate a solid trithiocarbonate compound, wherein the trithiocarbonate compound is 2,2'-(thiocarbonylbis(sulfanediyl))diacetate represented by the structural formula:

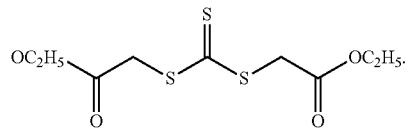 [SMILES: CCOC(=O)CSC(=S)SCC(=O)OCC]

2. The method for preparing a trithiocarbonate compound according to claim 1, wherein a molar ratio of ethyl cyanoacetate:carbon disulfide:ethyl chloroacetate is about 1:2:2, respectively.

3. The method for preparing a trithiocarbonate compound according to claim 1, wherein the organic solvent is dimethyl formamide.

4. The method for preparing a trithiocarbonate compound according to claim 1, further comprising recrystallizing the solid trithiocarbonate derivative precipitate from ethanol.

* * * * *